United States Patent [19]
Crainich et al.

[11] Patent Number: 6,053,908
[45] Date of Patent: Apr. 25, 2000

[54] RATCHET ASSEMBLY FOR SURGICAL INSTRUMENT

[75] Inventors: Lawrence Crainich, Charlestown; David Kangas, Claremont, both of N.H.

[73] Assignee: Design Standards Corporation, Charlestown, N.H.

[21] Appl. No.: 09/226,799

[22] Filed: Jan. 7, 1999

[51] Int. Cl.[7] ................................................. A61B 17/00
[52] U.S. Cl. ................................. 606/1; 606/139; 74/575
[58] Field of Search ................................. 606/69, 70, 71, 606/139, 142, 1; 74/575, 577 R, 578; 192/43.1

[56] References Cited

U.S. PATENT DOCUMENTS 3,232,089  2/1966  Samuels et al. ..................... 606/142
5,409,478  4/1995  Gerry et al. ........................... 606/1
5,732,806  3/1998  Foshee et al. ...................... 192/30 R

*Primary Examiner*—Michael Buiz
*Assistant Examiner*—David O. Reip
*Attorney, Agent, or Firm*—Bachman & LaPointe, P.C.

[57] ABSTRACT

A ratchet assembly for a surgical instrument includes a bar having teeth; a pawl having a member for engaging the teeth, the bar being movable relative to the pawl in two directions along an axis, and the pawl being pivotable between a first ratchet position for allowing movement of the bar relative to the pawl in a first direction along the axis and a second ratchet position for allowing movement of the bar relative to the pawl in a second direction along the axis; and a toggle member associated with the pawl and the bar for allowing pivot of the pawl between the first ratchet position and the second ratchet position.

17 Claims, 3 Drawing Sheets

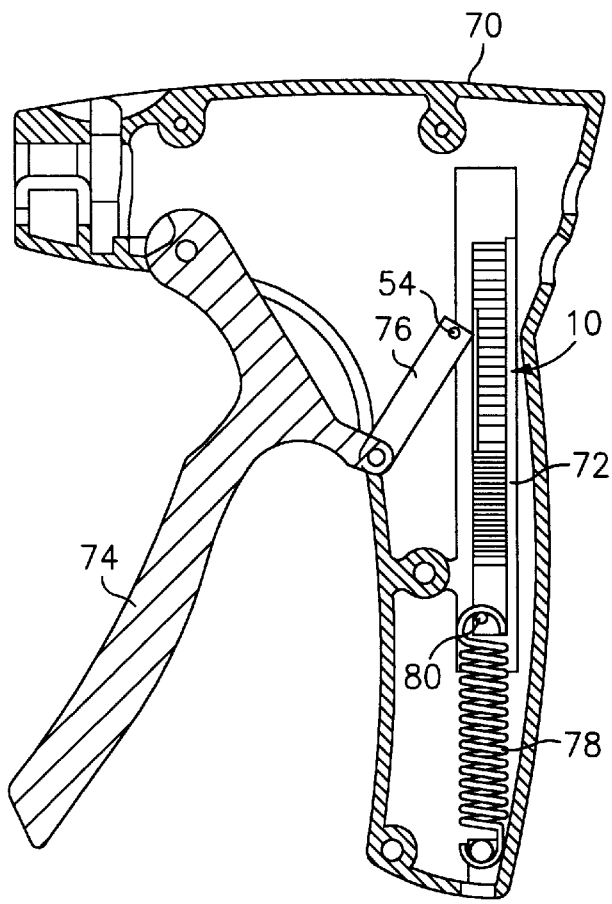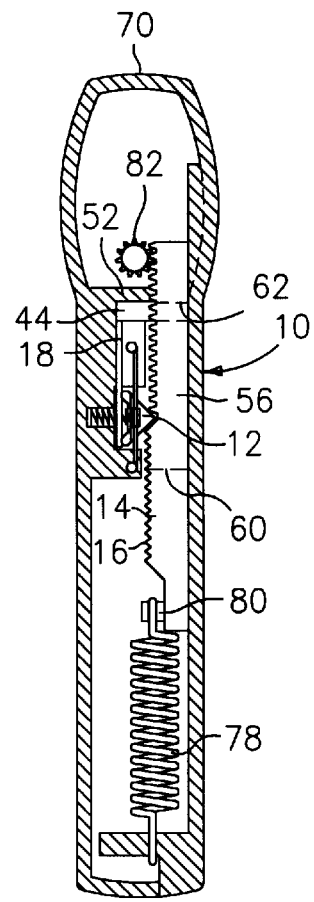
FIG. 9  FIG. 10
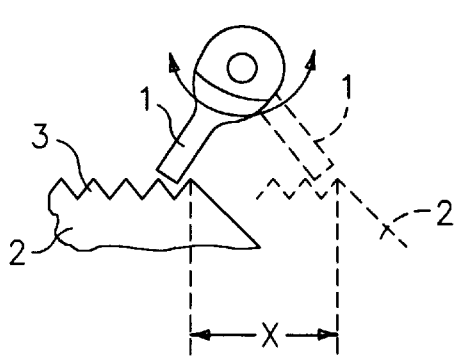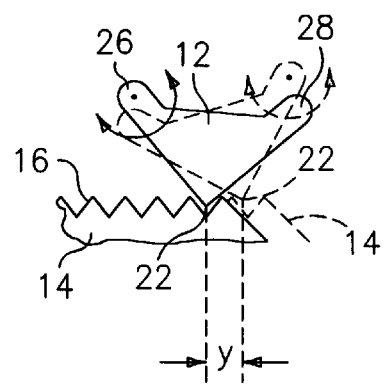
FIG. 11
(PRIOR ART)
FIG. 12

RATCHET ASSEMBLY FOR SURGICAL INSTRUMENT

BACKGROUND OF THE INVENTION

The invention relates to a ratchet assembly for a surgical instrument, more particularly to a ratchet assembly allowing alternating two-directional ratcheting with enhanced reliability and less unengaged motion during changeover from ratchet in one direction to the other.

Ratchet devices are known for use in surgical instruments for allowing incremental movement or pivot, for example of a trigger member, through a stroke in one direction followed by changeover to ratchet along a stroke in the opposite direction. FIG. 1 illustrates a prior art configuration wherein a pawl 1 is pivotably positioned for engaging a bar or rack 2 having teeth 3. When rack 2 is moved relative to pawl 1, pawl 1 engages rack 2 against reverse movement until rack 2 has moved entirely past pawl 1, at which point pawl 1 pivots to a neutral position and return movement of rack 2 engages pawl 1 in the opposite position. As shown, pawl 1 is a single extending member pivotable around a single point spaced from the tooth engaging portion of pawl 1. This is disadvantageous in that there is a noticeable distance along which rack 2 must be moved relative to pawl 1 to allow sufficient space for pawl 1 to pivot into the proper position for ratcheting in the opposite direction. During this movement, pawl 1 and rack 2 are not engaged.

In addition, no positive structure is provided in this prior art device for insuring that the pawl is positioned in the proper position and will engage teeth 3 of rack 2 as desired.

Thus, it is clear that the need remains for a ratchet structure which is more reliable and has reduced or eliminated unengaged movement during the switchover from ratchet in one direction to ratchet in the other direction.

It is therefore the primary object of the present invention to provide a ratchet assembly which reliably provides two-directional ratcheting.

It is a further object of the present invention to provide a ratchet assembly which exhibits minimal unengaged movement during switchover from ratcheting in one direction to ratcheting in the other direction.

It is a still further object of the present invention to provide a surgical instrument including a ratchet assembly in accordance with the present invention.

It is another object of the present invention to provide a ratchet assembly and surgical instrument incorporating same which is simple in manufacture.

Other objects and advantages of the present invention will appear hereinbelow.

SUMMARY OF THE INVENTION

In accordance with the present invention, the foregoing objects and advantages have been readily attained.

According to the invention, a ratchet assembly for a surgical instrument is provided, comprising a bar having teeth; a pawl having a member for engaging said teeth, said bar being movable relative to said pawl in two directions along an axis, and said pawl being pivotable between a first ratchet position for allowing movement of said bar relative to said pawl in a first direction along said axis and a second ratchet position for allowing movement of said bar relative to said pawl in a second direction along said axis; and a toggle member associated with said pawl and said bar for allowing pivot of said pawl between said first ratchet position and said second ratchet position.

Still further according to the invention, a ratchet assembly is provided which ratchet assembly comprises a bar having teeth; a pawl having a tooth engaging member for engaging said teeth, said pawl having a triangular configuration defined by said tooth engaging member, a first pivot member spaced from said tooth engaging member, and a second pivot member spaced from said tooth engaging member and said first pivot member, said bar being moveable relative to said pawl in two directions along an axis; and means for positioning said pawl relative to said bar in a neutral position and allowing pivot of said pawl around said first pivot member to a first ratchet position allowing movement of said bar relative to said pawl in one of said two directions, and allowing pivot of said pawl around said second pivot member to a second ratchet position allowing movement of said bar relative to said pawl in the other of said two directions.

In still further accordance with the present invention, a surgical instrument having a two-directional ratcheting structure is provided, which instrument comprises a housing; an operable element connected to said housing; an actuating member moveably mounted relative to said housing for operating said operable element; and a ratchet assembly associated with said actuating member for allowing alternating two-directional ratcheting of said actuating member relative to said housing, said ratchet assembly comprising a bar having teeth; a pawl having a member for engaging said teeth, said bar being movable relative to said pawl in two directions along an axis, and said pawl being pivotable between a first ratchet position for allowing movement of said bar relative to said pawl in a first direction along said axis and a second ratchet position for allowing movement of said bar relative to said pawl in a second direction along said axis and a toggle member associated with said pawl and said bar for allowing pivot of said pawl between said first ratchet position and said second ratchet position.

BRIEF DESCRIPTION OF THE DRAWINGS

A detailed description of preferred embodiments of the present invention follows, with reference to the attached drawings, wherein:

FIG. 9 is a cross-sectional side view of a surgical instrument including a ratchet assembly in accordance with the present invention;

FIG. 10 is an end sectional view of the surgical instrument of FIG. 9;

FIG. 11 illustrates operation of a prior art pawl; and

FIG. 12 illustrates operation of a pawl in accordance with the present invention.

DETAILED DESCRIPTION

The invention relates to a ratchet assembly for a surgical instrument, and a surgical instrument incorporating the ratchet assembly, whereby reliable two-directional ratcheting is provided with very little unengaged movement during switchover from ratcheting in one direction to ratcheting in the other direction.

Figure 1:
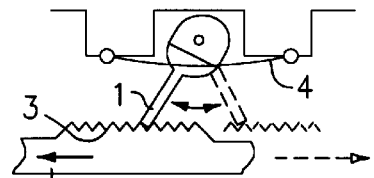
FIG. 1 illustrates a prior art ratcheting mechanism.

FIG. 1 illustrates a prior art ratcheting structure as discussed above. As shown, a typical prior art ratchet structure includes a pawl 1 and a bar or rack 2 carrying teeth 3 which are engaged by pawl 1 during ratcheting. FIG. 1 shows in solid lines a rack 2 being moved relative to pawl 1 in a left direction, wherein pawl 1 ratchets along teeth 3 as desired. After rack 2 has been moved entirely to the left beyond pawl 1, pawl 1 pivots to a neutral position to which it is biased by a wire spring 4. When rack 2 is moved in the other direction, pawl 1 is pivoted to the position shown in dashed lines in FIG. 1 so as to allow ratcheting in the other direction. Two specific disadvantages of this structure are that the positioning of pawl 1 relative to rack 2 relies solely upon movement of pawl 1 through contact with rack 2. In addition, a relatively large degree of motion is provided between switchover from leftward movement of rack 2 relative to pawl 1 to rightward movement, wherein pawl 1 has not engaged any teeth 3 of rack 2. This unengaged motion is undesirable.

In accordance with the present invention, a ratchet mechanism is provided which is reliable, which has additional structure for insuring proper positioning of a pawl member relative to a rack or bar carrying teeth, and which has substantially reduced unengaged motion during changeover from ratcheting in one direction to ratcheting in the other direction.

Figure 2:
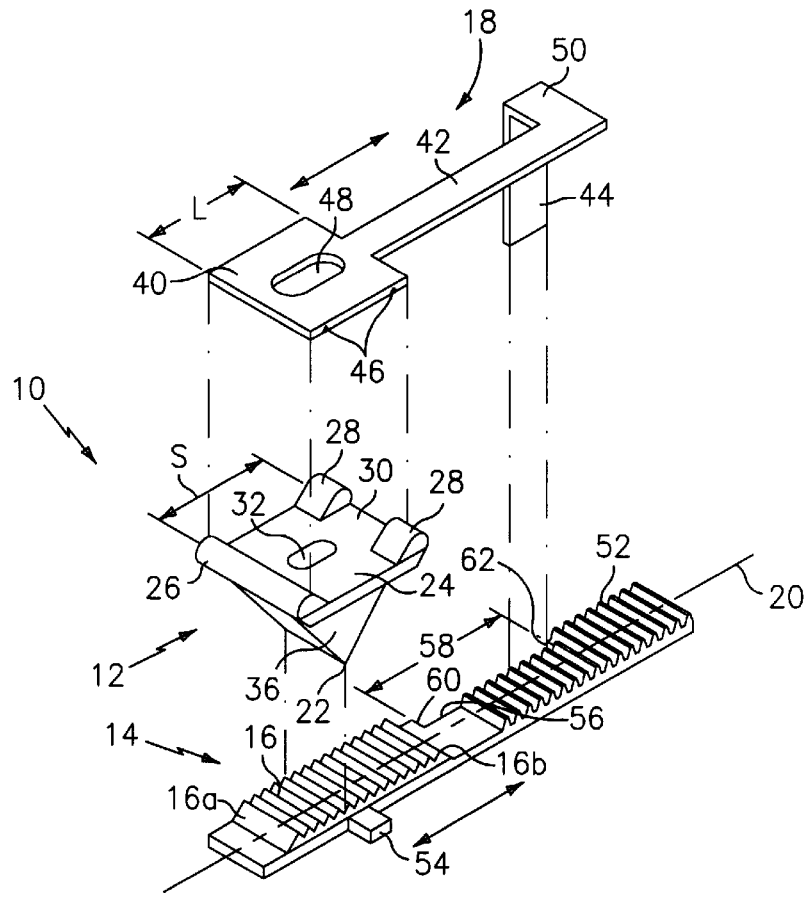
FIG. 2 is an exploded view of a ratchet assembly in accordance with the present invention.

FIG. 2 shows an exploded perspective view of a ratchet assembly 10 in accordance with the present invention. As shown, assembly 10 includes a pawl member 12, a bar or rack 14 carrying a series of teeth 16 to be engaged by pawl 12, and a toggle member 18 which, as will be thoroughly discussed below, is associated with bar 14 and pawl 12 so as to allow positioning or pivot of pawl 12 to desired ratchet positions for allowing ratcheting movement of bar 14 relative to pawl 12 along axis 20 in alternating directions.

Figure 3:
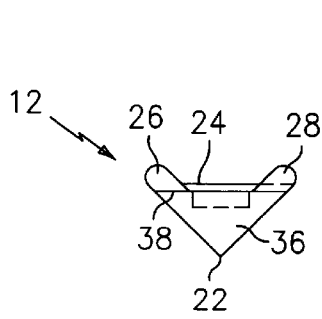
FIG. 3 is a side view of a pawl member in accordance with the present invention.
Figure 4:
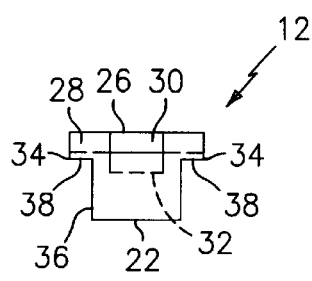
FIG. 4 is an end view of a pawl member in accordance with the present invention.
Figure 5:
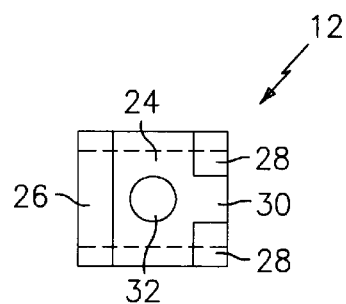
FIG. 5 is a top view of a pawl member in accordance with the present invention.

In accordance with the present invention, and as illustrated in FIGS. 2–5, pawl 12 according to the present invention has a tooth engaging member 22 which may come to a point, or a squared surface, or any other shape which may be desired for reliably engaging teeth 16. Pawl 12 also preferably includes a substantially squared flat surface opposite from tooth engaging member 22. Flat surface 24 is preferably provided with two spaced pivot members 26, 28, which may advantageously be rounded portions extending beyond flat surface 24. Pawl 12 may suitably have a substantially triangular cross-section from one side, for example as illustrated in FIG. 3, which triangular shape is preferably defined between tooth engaging member 22 and pivot members 26, 28. Pawl 23 may further suitably have a substantially square cross-section from the other side as illustrated in FIG. 4 so as to define tooth engaging member 22 having a substantial width for reliable engagement with teeth 16.

One pivot member 28 is preferably provided having a gap 30 for slidably receiving toggle member 18 as will be more thoroughly described below. A well 32 or recessed area is also preferably provided on pawl 12 for receiving a spring or other biasing member for biasing pawl 12 toward an engaging position with teeth 16.

As best shown in FIGS. 3 and 4, pawl 12 may also preferably be provided having flanges 34 extending outwardly from sides 36 of pawl 12 so as to define substantially flat surfaces 38 which can be used to help secure pawl 12 within a housing of a surgical instrument as desired.

Figure 6:
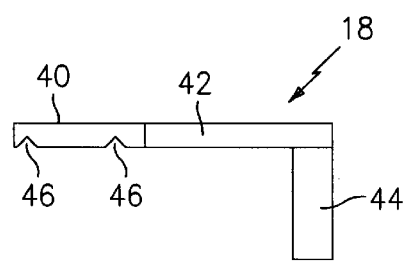
FIG. 6 is a side view of a toggle member in accordance with the present invention.
Figure 7:
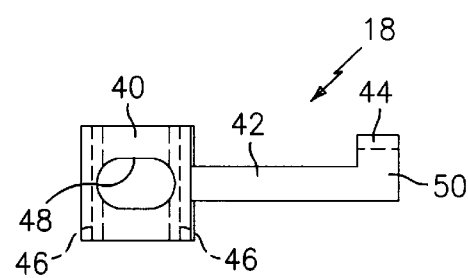
FIG. 7 is a top view of a toggle member in accordance with the present invention.

Referring to FIGS. 2, 6 and 7, toggle member 18 may suitably include a plate or head portion 40, a body member 42 and a bar engaging member 44. Plate 40 may suitably have a length L which is smaller than the spacing S between pivot members 26, 28. This configuration advantageously allows for plate 40 to be positioned relative to pawl 12 in one position where pivot member 26 is engaged and pivot member 28 can be rearwardly deflected, and a second position where pivot member 28 is engaged by plate 40 and pivot member 26 can be rearwardly deflected.

Plate 40 also preferably has two spaced notches 46 on one side thereof, and facing pivot members 26, 28. Notches 46 receive one pivot member 26, 28 in each of the positions of toggle member 18 relative to pawl 12 to allow stable pivot around pivot members 26, 28 respectively. Plate 40 also preferably has a cutout 48 which, when assembled, substantially overlies well 32 of pawl 12 so as to allow a biasing member to extend therethrough.

Body member 42 of toggle member 18 may suitably be provided having a substantially elongate flat structure which is desirable so as to provide stable slidable mounting within a housing of a surgical instrument. Body member 42 may suitably be provided having a transverse extension 50, and bar engaging member 44 may suitably extend, preferably substantially perpendicularly as shown in FIG. 2, from transverse extension 50. Extension 50 allows for proper positioning of bar engaging member 44 relative to bar 14.

Bar 14 as discussed above preferably includes teeth 16 arranged along a sufficient expanse of bar 14 to provide a desired range of ratcheting movement of bar 14 relative to pawl 12. At each end of the expanse of teeth 16, a last tooth 16a, 16b has an extended wall dropping to a lower region to allow for proper movement of pawl 12.

Bar 14 may preferably be provided having a series of gear engaging teeth 52 which may advantageously be engaged within a surgical instrument with an operable element such as a drive for surgical scissors, graspers, helical inserters, clip applicators, surgical staplers and the like. Bar 14 may also suitably be provided having a tab 54 or other structure which can be connected or otherwise engaged with a trigger or actuating member of a surgical instrument for imparting movement of bar 14 along axis 20. According to the invention, bar 14 is advantageously provided having a slot 56 or cutout which is sized to receive bar engaging member 44 of toggle member 18. Slot 56 preferably has a length 58 selected relative to the expanse of teeth 16 on bar 14 so that bar engaging member 44 contacts ends 60, 62 of slot 56 as pawl 12 ratchets off of the last tooth of teeth 16. This advantageously positions toggle member 18 relative to pawl 12 at the end of each full stroke of bar 14 relative to pawl 12.

When installed in a surgical instrument, bar 14 is preferably slidably mounted along axis 20 and engaged with a trigger or other member. Pawl member 12 is preferably secured within a receptacle or other enclosure in a housing of a surgical instrument so as to restrict movement in the direction of axis 20, and selectively allow pivot of pawl 12 around pivot points which substantially coincide with pivot members 26, 28.

Toggle member 18 is slidably positioned with plate 40 substantially adjacent to flat surface 24 and pivot members 26, 28, with bar engaging member 44 disposed in slot 56 of bar 14 and with body member 42 disposed in gap 30 of pivot member 28. In this manner, and as will be thoroughly discussed below, pawl 12 is positioned engaging pivot member 26 to allow ratcheting in one direction along axis 20 until bar 14 reaches an end point of movement in that direction, at which point toggle member 18 is positioned relative to pawl 12 so as to engage plate 40 with pivot member 28, thereby allowing pivot of pawl 12 around pivot member 28 to a position where reverse movement of bar 14 is allowed. Reverse movement of bar 14 will then cause such pivot around the engaged pivot member 28 to position pawl 12 in the proper position for ratcheting movement opposite to the original direction of ratchet. Obviously, ratchet assembly 10 of the present invention allows this process to be repeated as often as desired, with automatic toggling of pawl 12 between ratcheting positions at the end of each stroke.

Figure 8A:
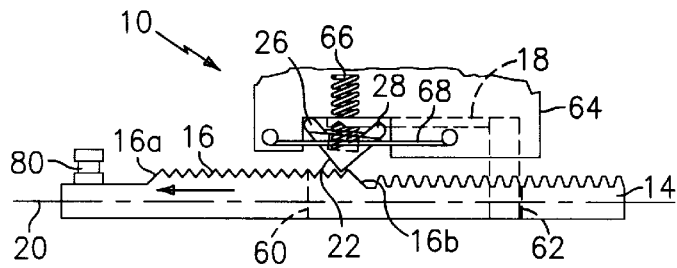
FIGS. 8*a–f* illustrate the two-directional operation of the ratchet structure in accordance with the present invention.

Referring to FIGS. 8a–f, this operation of the present invention as well as the mounting of pawl 12 within a surgical instrument will be illustrated. FIG. 8a shows pawl 12 mounted within an enclosure 64, with a biasing member 66 urging pawl 12 toward bar 14, and with a wire spring or stop member 68 secured along enclosure 64 so as to engage flat surfaces 38 defined by flanges 34 of pawl 12 and hold pawl 12 within enclosure 64 as desired. Toggle member 18 is slidably positioned with plate 40 behind pivot members 26, 28 within enclosure 64, and with bar engaging member 44 positioned in slot 56 of bar 14.

FIG. 8a shows pawl 12 having pivot member 28 engaged with plate 40, particularly within one notch 46 of plate 40, and pivot member 26 freely pivoting backward around a pivot point defined by engaged pivot member 28 so as to position pawl 12 in proper position for allowing ratchet of bar 14 to the left relative to pawl 12 as indicated by the arrow in the figure.

Figure 8B:
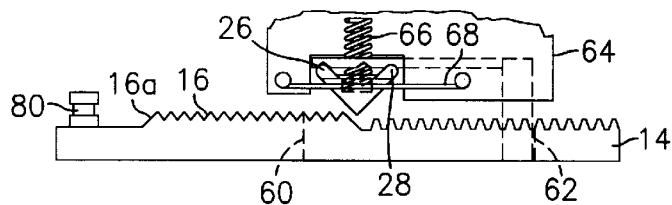

FIG. 8b shows assembly 10 at a point where bar 14 has been fully ratcheted to a left-most position, and pawl 12 has ratcheted past the last tooth 16a of teeth 16. In this position, biasing member 66 urges pawl 12 to a neutral position as shown, with flat surface 38 contacting wire spring 68. Further, at this point, bar engaging member 44 of toggle member 18 has been contacted by end 60 of slot 56 and moved relative to pawl 12 so as to engage a notch 46 of plate 40 with pivot member 26 as shown, and to release pivot member 28.

Figure 8C:
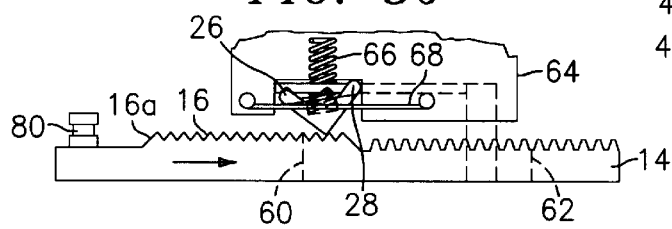

From this neutral position of pawl 12, bar 14 can now be ratcheted relative to pawl 12 to the right as shown in FIG. 8c, and when last tooth 16a contacts and moves past tooth engaging member 22 of pawl 12, pawl 12 now pivots around engaged pivot member 26 into the proper position for allowing further ratchet of bar 14 relative to pawl 12 to the right as shown by the arrow in FIG. 8c.

Figure 8D:
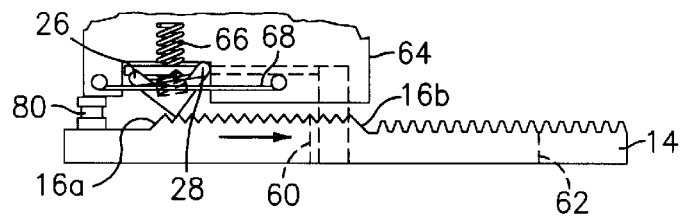
Figure 8E:
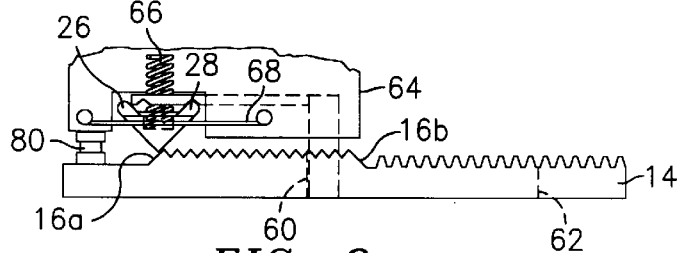

FIG. 8d shows bar 14 approaching the right-most position, and FIG. 8e shows bar 14 having reached the right-most position, where pawl 12 has ratcheted past last tooth 16b and is urged by biasing member 66 back to the neutral position, and bar engaging member 44 has been contacted by the other end 62 of slot 56 and moved again so as to engage pivot member 28 and release pivot member 26 as desired.

Figure 8F:
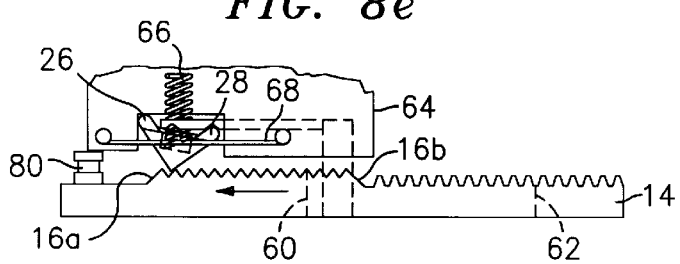

As shown in FIG. 8f, movement of bar 14 back to the left relative to pawl 12 will then cause pivot of pawl 12 around pivot member 28 and into the proper position for allowing ratchet only to the left as shown by the arrow in FIG. 8f.

From this series of illustrations, it should readily be appreciated that assembly 10 in accordance with the present invention advantageously allows two-directional ratchet of bar 14 relative to pawl 12 with a reliable engagement of pawl 12 with teeth 16, and further with very little unengaged movement during the transition from left ratchet to right ratchet. This is due to the fact that pivot of pawl 12 between the positions for allowing left and right ratchet is very small, and is conducted from the neutral position around two separate points. This is in clear distinction to the pivot of prior art devices as illustrated, for example, in FIG. 1.

FIGS. 9 and 10 illustrate ratchet assembly 10 within a housing 70 of a typical surgical instrument. FIGS. 9 and 10 show bar 14 slidably positioned along a track 72 within housing 70, and connected to a trigger member 74 through a bar 76 which may, for example, be pivotably connected to tab 54 and trigger 74 so that pivot of trigger 74 linearly translates bar 14 as desired. Bar 14 may suitably be biased toward one position by a spring 78 which may be fixed within housing 70 at one end, and engaged around a knob 80 of bar 14 at the other end. FIG. 10 shows bar 14 having gear engaging teeth 52 engaged with a gear 82 which, as discussed, may suitably be connected to an operable element of the surgical instrument so that pivot of trigger 74 operates the operable element through ratchet assembly 10 of the present invention. FIG. 10 also shows installation of pawl 12 within enclosure 64 and including biasing member 66 and wire spring 68, and toggle member 18 with plate 40 behind pawl 12 in enclosure 64, and with bar engaging member 44 disposed in slot 56.

In order to further highlight the advantages of the present invention, FIGS. 11 and 12 are presented and comparatively show the unengaged movement of the ratchet bar relative to the pawl in a prior art configuration and with the configuration of the present invention.

FIG. 11 shows a prior art apparatus and shows in solid lines a left-most ratchet position, and in dashed lines the unengaged movement back toward the right which must be traversed before pawl 1 engages teeth 3. The unengaged distance with this configuration is shown at X.

Referring to FIG. 12, the left-most position of bar 14 relative to pawl 12 of the ratchet assembly 10 of the present invention is shown in solid lines, and the rightward movement of bar 14 relative to pawl 12 which is necessary to reengage tooth engaging member 22 with teeth 16 is shown at Y. Clearly, the apparatus of the present invention provides for far less unengaged movement during transition or switchover from ratchet in one direction to ratchet in the other. This is due to the double-pivoting of pawl 12 of the present invention, wherein pawl 12 pivots from a neutral position to one ratcheting position around one pivot member 26, and to the other ratcheting position around the other pivot member 28.

In the embodiment illustrated herein, toggle member 18 is moveable along a toggle stroke by movement of bar 14, and the toggle stroke is shorter than the stroke of bar 14. This is advantageous as a short stroke for toggle member 18 provides a more stable and reliable device. Of course, other configurations are possible and well within the scope of the invention.

It should readily be appreciated that, in accordance with the present invention, a ratchet assembly has been provided which advantageously allows reliable ratcheting in two directions along the stroke or degree of movement of a trigger or other actuating member. This assembly may advantageously be incorporated into a wide variety of surgical or other instruments, such as surgical scissors, graspers, clip applicators, helical inserters, surgical staplers and the like.

It is to be understood that the invention is not limited to the illustrations described and shown herein, which are deemed to be merely illustrative of the best modes of carrying out the invention, and which are susceptible to modification of form, size, arrangement of parts and details of operation. The invention rather is intended to encompass all such modifications which are within its spirit and scope as defined by the claims.

We claim:

1. A ratchet assembly for a surgical instrument, comprising:

a bar having teeth;

a pawl having a member for engaging said teeth, said bar being movable relative to said pawl in two directions along an axis, and said pawl being pivotable between a first ratchet position for allowing movement of said bar relative to said pawl in a first direction along said axis and a second ratchet position for allowing movement of said bar relative to said pawl in a second direction along said axis; and a toggle member associated with said pawl and said bar for selectively allowing pivot of said pawl between said first ratchet position and said second ratchet position.

2. A ratchet assembly according to claim 1, wherein said teeth extend along said bar and have a first end and a second end, and wherein said toggle member is arranged relative to said bar and said pawl so as to pivot said pawl between said first ratchet position and said second ratchet position when said pawl reaches said first end and said second end respectively.

3. A ratchet assembly according to claim 1, further comprising means for biasing said pawl against said teeth.

4. A ratchet assembly according to claim 1, further comprising at least one pivot member positioned on one of said pawl and said toggle member and contacting the other of said pawl and said toggle member, and wherein said toggle member is moveable relative to said pawl between a first position wherein said pivot member allows said pawl to pivot to said first ratchet position, and a second position wherein said pivot member allows said pawl to pivot to said second ratchet position.

5. A ratchet assembly according to claim 4, wherein said toggle member is moved between said first position and said second position by said bar.

6. A ratchet assembly according to claim 1, wherein said bar is moveable relative to said pawl along an operative stroke, and wherein said toggle member is moveable relative to said pawl by said bar along a toggle stroke shorter than said operative stroke.

7. A ratchet assembly according to claim 1, wherein said toggle member includes a bar engaging member, and wherein said bar includes a slot having ends and slidably receiving said bar engaging member whereby movement of said bar along said axis moves said bar relative to said toggle member until said bar engaging member contacts one of said ends of said slot, and further movement of said bar member moves said toggle member.

8. A ratchet assembly according to claim 4, wherein the at least one pivot member comprises first and second spaced pivot members positioned on said pawl, and said toggle member includes a plate contacting said first pivot member in said first position and contacting said second pivot member in said second position.

9. A ratchet assembly according to claim 8, wherein said plate includes at least one notch engaging said first pivot member in said first position and engaging said second pivot member in said second position.

10. A ratchet assembly according to claim 1, wherein said pawl is pivotably disposed in a housing, and further comprising a stop member for holding said pawl in said housing, and means for biasing said pawl against said stop member.

11. A ratchet assembly according to claim 10, wherein said means for biasing urges said pawl toward a neutral position, and said toggle member is slidable relative to said pawl to selectively allow pivot of said pawl from said neutral position to said first ratchet position and said second ratchet position.

12. A ratchet assembly according to claim 1, wherein said toggle member is moveable relative to said pawl between a first position allowing pivot of said pawl to said first ratchet position and a second position allowing pivot of said pawl to said second ratchet position, wherein said bar is moveable along said axis between a first end point and a second end point, wherein movement of said bar to said first end point moves said toggle member to said first position, wherein subsequent movement of said bar toward said second end point pivots said pawl to said first ratchet position, wherein movement of said bar to said second end point moves said toggle member to said second position, and wherein subsequent movement of said bar toward said first end point pivots said pawl to said second ratchet position.

13. A ratchet assembly, comprising:

a bar having teeth;

a pawl having a tooth engaging member for engaging said teeth, said pawl having a triangular configuration defined by said tooth engaging member, a first pivot member spaced from said tooth engaging member, and a second pivot member spaced from said tooth engaging member and said first pivot member, said bar being moveable relative to said pawl in two directions along an axis; and means for positioning said pawl relative to said bar in a neutral position and allowing pivot of said pawl around said first pivot member to a first ratchet position allowing movement of said bar relative to said pawl in one of said two directions, and allowing pivot of said pawl around said second pivot member to a second ratchet position allowing movement of said bar relative to said pawl in the other of said two directions.

14. A surgical instrument having a two-directional ratcheting structure, comprising:

a housing;

an operable element connected to said housing;

an actuating member moveably mounted relative to said housing for operating said operable element; and a ratchet assembly associated with said actuating member for allowing alternating two-directional ratcheting of said actuating member relative to said housing, said ratchet assembly comprising:

a bar having teeth;

a pawl having a member for engaging said teeth, said bar being movable relative to said pawl in two directions along an axis, and said pawl being pivotable between a first ratchet position for allowing movement of said bar relative to said pawl in a first direction along said axis and a second ratchet position for allowing movement of said bar relative to said pawl in a second direction along said axis; and a toggle member associated with said pawl and said bar for allowing pivot of said pawl between said first ratchet position and said second ratchet position.

15. A surgical instrument according to claim 14, wherein said bar is slidably mounted in said housing and moveable along said axis by said actuating member.

16. A surgical instrument according to claim 14, wherein said housing further comprises a pawl housing structure, said pawl being pivotably disposed in said pawl housing structure, and further comprising a stop member for holding said pawl in said pawl housing structure, and means for biasing said pawl against said stop member.

17. A surgical instrument according to claim 14, wherein said toggle member is moveable relative to said pawl between a first position allowing pivot of said pawl to said first ratchet position and a second position allowing pivot of said pawl to said second ratchet position, wherein said bar is moveable along said axis between a first end point and a second end point, wherein movement of said bar to said first end point moves said toggle member to said first position, wherein subsequent movement of said bar toward said second end point pivots said pawl to said first ratchet position, wherein movement of said bar to said second end point moves said toggle member to said second position, and wherein subsequent movement of said bar toward said first end point pivots said pawl to said second ratchet position.

* * * * *